(12) United States Patent
Angeletakis

(10) Patent No.: US 6,384,106 B1
(45) Date of Patent: *May 7, 2002

(54) DENTAL RESTORATIVE COMPOSITE

(75) Inventor: Christos Angeletakis, Orange, CA (US)

(73) Assignee: Kerr Corporation, Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/562,190

(22) Filed: May 2, 2000

Related U.S. Application Data

(62) Division of application No. 09/093,778, filed on Jun. 9, 1998, now Pat. No. 6,127,450.

(51) Int. Cl.⁷ .............................................. A61K 6/083
(52) U.S. Cl. ..................... 523/116; 523/115; 433/228.1
(58) Field of Search ................................. 523/116, 117, 523/118, 115; 433/228.1

(56) References Cited

U.S. PATENT DOCUMENTS

| | | |
|---|---|---|
| 3,859,421 A | 1/1975 | Hucke |
| 4,164,794 A | 8/1979 | Spector et al. |
| 4,197,234 A | 4/1980 | Temin |
| 4,292,029 A | 9/1981 | Craig et al. |
| 4,345,057 A | 8/1982 | Yamabe et al. |
| 4,362,681 A | 12/1982 | Spector et al. |
| 4,396,476 A | 8/1983 | Roemer et al. |
| 4,407,984 A | 10/1983 | Ratcliffe et al. |
| 4,411,625 A | 10/1983 | Koblitz et al. |
| 4,433,958 A | 2/1984 | Fellman et al. |
| 4,499,251 A | 2/1985 | Omura et al. |
| 4,514,174 A | 4/1985 | Dougherty et al. |
| 4,515,930 A | 5/1985 | Omura et al. |
| 4,525,493 A | 6/1985 | Omura et al. |
| 4,537,940 A | 8/1985 | Omura et al. |
| 4,539,382 A | 9/1985 | Omura et al. |
| 4,544,683 A | 10/1985 | Müller et al. |
| 4,547,531 A | 10/1985 | Waknine |
| 4,612,384 A | 9/1986 | Omura et al. |
| 4,650,847 A | 3/1987 | Omura et al. |
| 4,722,947 A | 2/1988 | Thanawalla et al. |
| 4,745,138 A | 5/1988 | Thanawalla et al. |
| 4,756,862 A | 7/1988 | Spector et al. |
| 4,813,875 A | 3/1989 | Hare |
| 4,839,401 A | 6/1989 | Waknine |
| 4,846,165 A | 7/1989 | Hare et al. |
| 4,857,111 A | 8/1989 | Haubennestel et al. |
| 4,952,613 A | 8/1990 | Hosoda |
| 4,957,554 A | 9/1990 | Mathers et al. |
| 5,125,971 A | 6/1992 | Nonami et al. |
| 5,130,463 A | 7/1992 | Haubennestel et al. |
| 5,134,175 A | 7/1992 | Lucey |
| 5,151,218 A | 9/1992 | Haubennestel et al. |
| 5,171,147 A | 12/1992 | Burgess |
| 5,180,757 A | 1/1993 | Lucey |
| 5,399,782 A | 3/1995 | Leppard et al. |
| 5,501,827 A | 3/1996 | Deeney et al. |
| 5,534,559 A | 7/1996 | Leppard et al. |
| 5,536,871 A | 7/1996 | Santhanam |
| 5,583,178 A | 12/1996 | Oxman et al. |
| 5,596,025 A | 1/1997 | Oxman et al. |
| 5,661,222 A | 8/1997 | Hare |
| 5,674,513 A | 10/1997 | Snyder, Jr. et al. |
| 5,697,390 A | 12/1997 | Garrison et al. |
| 5,708,051 A | 1/1998 | Erdrich et al. |
| 5,760,102 A | 6/1998 | Hall et al. |
| 5,830,951 A | 11/1998 | Fiedler |
| 5,843,348 A | 12/1998 | Giordano |
| 5,847,025 A | 12/1998 | Moszner et al. |
| 5,849,270 A | 12/1998 | Podszun et al. |
| 5,861,445 A | 1/1999 | Xu et al. |
| 6,127,450 A * | 10/2000 | Angeletakis ................. 523/116 |

FOREIGN PATENT DOCUMENTS

| | | |
|---|---|---|
| WO | WO 98/36729 | 8/1998 |

\* cited by examiner

*Primary Examiner*—Peter Szekely
(74) *Attorney, Agent, or Firm*—Wood, Herron & Evans, LLP

(57) ABSTRACT

The present invention provides a resin-based dental restorative that exhibits high condensability, low volumetric shrinkage and low shrinkage stress. To this end, one or more of a rheological modifier, dispersant and fluorocopolymer are mixed with a methacrylate resin and a fine mineral filler in amounts effective to improve the condensability of the resulting composite to achieve amalgam-like condensation, to reduce the volumetric shrinkage to less than about 2% during polymerization, to improve wear resistance, and to provide a composite with generally improved physical properties.

16 Claims, No Drawings

DENTAL RESTORATIVE COMPOSITE

CROSS REFERENCE TO RELATED APPLICATION

This application is a divisional of U.S. patent application Ser. No. 09/093,778 filed Jun. 9, 1998, and entitled DENTAL RESTORATIVE COMPOSITE.

FIELD OF THE INVENTION

This invention relates to resin-based dental restoratives, and more specifically to restorative compositions that exhibit high condensability, low volumetric shrinkage and improved wear/abrasion resistance.

BACKGROUND OF THE INVENTION

Posterior and anterior tooth restoration is typically accomplished by excavating a tooth that has decayed or is otherwise in need of repair to form a cavity. This cavity is filled with a paste material, which is then compacted and shaped to conform to the original contour of the tooth. The paste is then hardened, typically by exposure to actinic light. The paste material is a tooth colored, packable, light curable, polymerizable restorative composition comprising a highly filled material.

Posterior tooth restorations, especially the Class II type, require the use of a matrix band for proper application of a restorative. The restorative has to be condensable. That is, as it is packed into the cavity of a tooth surrounded by a matrix band, the restorative must deform the matrix band in such a way that the original tooth contour is achieved. In addition, proper deformation of the matrix band leads to appropriate contact with the adjacent teeth.

Up to now, the only type of restorative having adequate rheological properties for use with a matrix band has been amalgam. Amalgams have been employed as restoratives for this purpose for a long time and they are known to have good wear characteristics, good marginal quality over time due to buildup of corrosion products at the border of the restoration and a small coefficient of thermal expansion. The metallic color, however, is a drawback for their use as is the uncertainty of the biological interactions of the metallic components of dental amalgams.

Tooth colored dental restorative composites are usually composed of dispersions of glass filler particles below 50 $\mu$m in methacrylate-type monomer resin. Splintered pre-polymerized particles, which are ground suspensions of silica in pre-polymerized dental resins, may also be used. Additives such as pigments, initiators and stabilizers have also been used in these types of composites. Because the glass particle surface is generally hydrophilic, and because it is necessary to make it compatible with the resin for mixing, the glass filler is treated with a silane to render its surface hydrophobic. The silane-treated filler is then mixed with the resin at a proportion (load) to give a paste with a consistency considered usable, that is to allow the paste to be shaped without it flowing under its own weight during typical use. This paste is then placed on the tooth to be restored, shaped and cured to a hardened mass by chemical or photochemical initiation of polymerization. After curing, the mass has properties close to the structure of a tooth.

Although it has been found that increasing the load of a resin-based composite leads to higher viscosity, amalgam-like condensability has not yet been achieved. There is thus a need in the dental profession to have a resin-based restorative that is condensable and compatible with the use of a matrix band.

As stated previously, the resins typically used in dental restorative compositions are mostly comprised of dimethacrylate monomers. These monomers vitrify quickly upon initiation of polymerization by crosslinking. The added glass particles after polymerization give a higher modulus to the system and reduce crack propagation by dispersion reinforcement.

A significant disadvantage in the use of methacrylate resin-based restorative composites is that they shrink significantly after cure. For example, a modern hybrid composite shrinks approximately 3% after cure. This shrinkage leads to further tooth decay because bacterial infiltration is possible. To address the problem of tooth decay, adhesives are used to coat the tooth surface to be restored before the application of the composite. The shrinkage stress during the initial phase of the vitrification process, however, is significant and on the order of 1 MPa or higher during the first 20 seconds of light exposure for a light cure composite. This initial stress development compromises the performance of the adhesive. So even with the use of an adhesive, significant marginal breakdown can occur, leading to bacterial infiltration. This process is defined as microleakage and is usually measured by dye penetration methods. Thus, there is also a need to make available to the dental profession a resin-based composite that has reduced volumetric shrinkage and shrinkage stress.

The coefficient of thermal expansion of the glass fillers used in resin-based composites is much closer to tooth structure than that of the resins. So it is desirable to limit the amount of the resin in a dental composite and maximize the amount of filler material. The main factor limiting the volume fraction (load) of the inorganic filler in highly filled suspensions is particle-particle interactions. Dispersants, through their ability to reduce interactions between particles can improve the flow (reduce the viscosity) of the suspension, therefore allowing a higher load. Dispersants in non-aqueous systems reduce particle interactions by a steric stabilization mechanism. A layer of the dispersant is adsorbed on the surface of the particles keeping them apart from one another, reducing the viscosity. The dispersant structure must contain a chain that allows for steric stabilization in the resin and it also must be strongly adsorbed on the particle surface. There is thus a further need to provide a dispersant that will be effective with a non-aqueous, highly filled suspension containing polymerizable groups for use in a dental restoration.

An additional critical area needing improvement in dental restorations is the wear and abrasion resistance of polymeric restorative compositions. For posterior restorations, the main wear mechanism is generally classified as the three body type, involving food bolus. For anterior restorations, wear is generally classified as the two body type, involving toothbrush abrasion, for example. Wear is caused by the heterogeneous nature of dental composites, occurring mostly through "plucking" of the filler particles from the surface followed by abrasion of the softer resin phase. Because wear in these systems is highly dependant on friction, friction reducing additives are expected to improve abrasion resistance. For example, in Temin U.S. Pat. No. 4,197,234, polytetrafluoroethylene powder or another similar polyfluorocarbon resin or polyfluorochlorocarbon resin is added for improvement of abrasion resistance in a chemically cured dental composite. The polytetrafluoroethylene additive or other similar additives, however, also act as an opacifying agent, making the restoration nonaesthetic. In other words, the color of the restoration does not blend sufficiently with the surrounding dentition. In addition, when the opacity is high, light cure initiation cannot be used. Similarly, Fellman et al. U.S. Pat. No. 4,433,958 describes the use of several fluoropolymers as solid particulate insoluble in the liquid monomer system in dental restorative formulations. Again, highly opaque materials are obtained.

There is thus an additional need to provide a dental restorative composite with superior wear and abrasion resistance in both posterior and anterior applications, without causing undue opacity in the restorative.

In summary, the dental profession is in need of a dental restorative that has improved shrinkage properties, higher load capabilities and superior wear and abrasion resistance, and that is condensable and compatible with the use of a matrix band.

SUMMARY OF THE INVENTION

The present invention provides a resin-based dental restorative that exhibits one or more of the following properties: high condensability, low volumetric shrinkage, low shrinkage stress, higher loading, lower coefficient of thermal expansion, and high wear and abrasion resistance. In its broadest form, the dental restorative composition of the present invention includes (1) a polymerizable (meth)acrylic monomer; (2) filler; and (3) one or more of the following additives: a rheological modifier in an amount effective to reduce the volumetric shrinkage of the dental restorative during polymerization/curing; a phosphate-based dispersant; and a fluorocopolymer that is soluble in (meth)acrylate resin.

Suitable rheological modifiers for use in the present invention include, among others, the following two types of compounds:

(1) a hydroxyfunctional polycarboxylic acid amide according to the formula

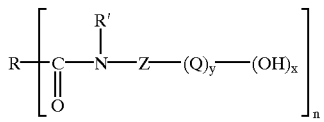

wherein the symbols have the following meanings:

R=aliphatic hydrocarbon groups having 6 to 60 carbon atoms, or aromatic hydrocarbon groups having 6 to 20 carbon atoms, or aliphatic or aliphatic/aromatic hydrocarbon radicals having 6 to 150 carbon atoms which are interrupted by 2, 4, 6 or 8 carboxamide groups, or aliphatic hydrocarbon radicals having 4 to 150 carbon atoms which are interrupted by 2 to 75 —O— (oxygen) groups;

R'=H, or $C_1$, to $C_4$ alkyl, or —Z'—$(Q)_y$—$(OH)_x$;

x=1 to 3;

y=0 or 1;

Z=an alkylene radical having 2 to 6 carbon atoms;

Z'=an alkylene radical which is identical to or different from Z, having 2 to 6 carbon atoms;

Q=an aliphatic hydrocarbon radical having 2 to 200 carbon atoms, which is linked via —O— or

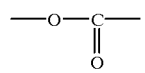

to Z or Z' and is interrupted by zero to 99 oxygen atoms and/or carboxylic acid ester groups; and n=2 to 3; and (2) the reaction product of:
 (a) from about 15 to 75 parts by weight of one or more liquid polyalkoxylated nitrogen-containing compounds containing more than one hydroxyl group and which also contain a pendant aliphatic radical of 6 to 40 carbon atoms selected from the group consisting of tertiary amines and amides of secondary amines;
 (b) from about 8 to 90 parts by weight of one or more polycarboxylic acids; and
 (c) from about 0.5 to 20 parts by weight of one or more liquid diamines of a molecular weight of about 2000 or less, wherein the reaction is continued until the acid value is within the range of 5 to 14 and the amine value is within the range of 42 to 84.

It has been found that the inclusion of either of the above rheological modifiers in the resin and filler composition of the present invention improves the condensability and shrinkage properties of the resulting composite. By way of example, but not limitation, if the first mentioned modifier is used it is preferably present in an amount of about 0.1 to about 0.7 weight percent, and if the second modifier is used it is preferably added in an amount of about 0.1 to about 1.5 weight percent of the total mixture.

Suitable phosphate-based dispersants for use in the present invention include, among others, the following types of compounds:

(1) a phosphoric acid ester according to the formula

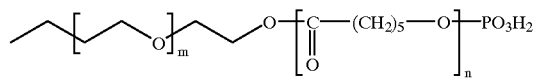

wherein n=5 to 10 and m=1 to 20; and (2) a phosphoric acid ester according to the formula

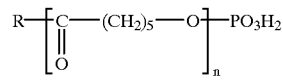

wherein R is a (meth)acrylate group functionalized radical. R is preferably one of the following radicals: oxyethyl methacryloyl-, oxyethyl acryloyl-, polyoxypropyl methacryloyl-, glyceryl dimethacryloyl-, and dipentaerythritol pentaacryloyl-. The inclusion of either of the above types of dispersants or a combination thereof in the resin and filler composition of the present invention increases the filler loading, which results in reduced shrinkage, a lower coefficient of thermal expansion and generally improved physical properties. The dispersant is preferably present in an amount of 5 weight percent or less of the total mixture.

One suitable fluorocopolymer for use in the present invention is soluble in (meth)acrylate resins and is comprised of about 40–60 mole percent fluoroolefin units, about 5–45 mole percent cyclohexyl vinyl ether units, about 5–45 mole percent alkyl vinyl ether units and about 3–15 mole percent hydroxyalkyl vinyl ether units. The inclusion of this type of fluorocopolymer reduces the wear of the composite material. The fluorocopolymer is preferably present in an amount of 10 weight percent or less of the total mixture.

There is thus provided a dental restorative having improved thixotropic and physical properties and improved wear resistance. These and other objects and advantages of the present invention shall become more apparent from the description of the preferred embodiments and the examples.

DETAILED DESCRIPTION

In connection with the present invention, it has been discovered that a) the addition of a suitable rheological modifier to a (meth)acrylate resin-based restorative composite improves the condensability and shrinkage properties of the resulting composite, without negatively impacting other critical properties; b) the addition of a suitable dispersant of the phosphoric acid ester type increases the filler loading, and after curing provides a composite with reduced shrinkage characteristics; c) the addition of a suitable fluorocopolymer reduces the wear of the composite without negatively impacting physical and aesthetic properties; and d) the addition of a combination of two or more of a suitable rheological modifier, dispersant and fluorocopolymer provides a dental restorative composite with improved condensability, shrinkage, wear, filler load and other physical and aesthetic properties.

Dental Restorative Composite with Rheological Modifier

Ordinarily, the restoration of posterior teeth, in particular Class II restoration, involves one or more side surfaces in addition to the top surface of the tooth. After preparation of the cavity, a matrix band is placed. The matrix band is a thin, malleable metal or plastic sheet designed to fit around the side surfaces of the tooth and designed to be capable of being tightened. Tightening the matrix band results in intimate contact with said tooth surfaces. Manipulation of the matrix band with dental instruments may then be necessary to achieve the original tooth contour. The filling of the tooth is accomplished by an opening at the top surface. When the tooth is filled with amalgam, the amalgam is condensed (compacted) in such a way as to deform the matrix band further to give a better approximation of the original contour of the tooth. Heretofore, this type of deformation has not been possible with previously available resin-based composites even though they have been recommended for use in posterior tooth restoration. It is believed that only by using the materials described in the present invention is amalgam-like condensation possible. This is accomplished by the addition of a rheological modifier to the resin and filler mixture. While various rheological modifiers known for non-dental applications were tested for use in dental restoratives of the present invention, it was found that only certain such modifiers provide the desired properties of increased condensability, lower volumetric shrinkage and reduced shrinkage stress:

One such modifier is Formula (1): a hydroxyfunctional polycarboxylic acid amide according to the formula

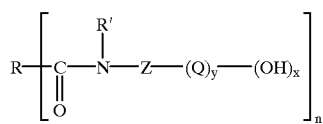

wherein the symbols have the following meanings:
R=aliphatic hydrocarbon groups having 6 to 60 carbon atoms, or aromatic hydrocarbon groups having 6 to 20 carbon atoms, or aliphatic or aliphatic/aromatic hydrocarbon radicals having 6 to 150 carbon atoms which are interrupted by 2, 4, 6 or 8 carboxamide groups, or aliphatic hydrocarbon radicals having 4 to 150 carbon atoms which are interrupted by 2 to 75 —O— (oxygen) groups;

R'=H, or $C_1$ to $C_4$ alkyl, or —Z'—(Q)$_y$—(OH)$_x$;

x=1 to 3;

y=0 or 1;

Z=an alkylene radical having 2 to 6 carbon atoms;

Z'=an alkylene radical which is identical to or different from Z, having 2 to 6 carbon atoms;

Q=an aliphatic hydrocarbon radical having 2 to 200 carbon atoms, which is linked via —O— or

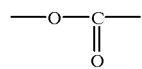

to Z or Z' and is interrupted by zero to 99 oxygen atoms and/or carboxylic acid ester groups; and n=2 to 3; and Another such modifier is Formula (2): the reaction product of:
(a) from about 15 to 75 parts by weight of one or more liquid polyalkoxylated nitrogen-containing compounds containing more than one hydroxyl group and which also contain a pendant aliphatic radical of 6 to 40 carbon atoms selected from the group consisting of tertiary amines and amides of secondary amines;
(b) from about 8 to 90 parts by weight of one or more polycarboxylic acids; and
(c) from about 0.5 to 20 parts by weight of one or more liquid diamines of a molecular weight of about 2000 or less, wherein the reaction is continued until the acid value is within the range of 5 to 14 and the amine value is within the range of 42 to 84.

It is believed that the Formula 1 modifier may be obtained from BYK Chemie USA, Wallingford, Conn., under the trade name BYK®-405. The Formula 2 modifier, it is believed, may be obtained from Rheox Corporation, Hightstown, N.J. under the trade name Thixatrol® VF-10. Either modifier has the effect of providing pseudoplastic and thixotropic properties to the composite pastes. These rheological modifiers and their thixotropic properties are described in U.S. Pat. Nos. 4,857,111 and 5,536,871, respectively, the entire disclosures of which are incorporated herein by reference. The condensable nature of the compositions containing either modifier, or both modifiers in combination, allows for the accomplishment of the contour without voids and gaps because the material offers resistance to packing. The condensable compositions of the present invention are also useful for those restorations not requiring a matrix band, such as Class I, III and V.

The rheological modifiers may be added directly during the mixing of the paste when the resin and the filler are combined in a planetary mixer. Alternatively, a solution of the rheological modifier in a volatile solvent, such as 10 percent modifier in ethanol, may be sprayed on the filler, followed by drying. This is the preferred method for formulating the rheological modifier into composites that are self-cured and powder-liquid. The modifier is added in an amount effective to achieve the desired properties of reduced volumetric shrinkage and shrinkage stress and improved condensability. This amount is variable depending on the compositions used for the resin and filler, but for example the range of 0.1 to 5 weight percent is contemplated. For the Formula 1 modifier the amount is likely to be in the range of about 0.1 to about 0.7 weight percent and about 0.1 to about 1.5 weight percent for the Formula 2 modifier. If too much modifier is added, the composite becomes too thick and will be difficult to manufacture and manipulate. If too little modifier is added, the desired effects will not be achieved. In a preferred embodiment of the present invention, 0.3 to 0.6 weight percent of Formula 1 modifier or 0.5 to 1.2 weight percent of Formula 2 modifier is added to the composite paste.

When the cavity to be filled is more than 2 mm deep, conventional light-cured resin-based composites must be layered with a layer thickness of 2 mm maximum in order to minimize the effects of the shrinkage occurring during polymerization. Because the compositions of the present invention show reduced shrinkage when cured and permit adequate depth of cure, the layering technique used during the placement of conventional light-cured resin-based composites can be eliminated or the layer thickness can be significantly increased, making placement simpler and less technique-sensitive when using the compositions of the present invention. The following examples will further illustrate the advantages of this aspect of the present invention.

EXAMPLE 1

One control sample and two test samples were prepared according to the following method. A methacrylate resin, as described in Table 1, was introduced in a planetary mixer and thermostated to 50° C. A rheological modifier according to Formula 1 was then added to the resin of test sample 2 and a rheological modifier according to Formula 2 was added to the resin of test sample 3. The mixer was started for about 5 minutes to mix the resin phase and then the filler containing the physically admixed components listed in Table 2 was slowly added over a period of 3–5 hours. Mixing was continued for another hour and the resultant paste was deaerated under attenuated oxygen pressure. Table 3 details the physical properties of the sample pastes prepared. All measurements were carried out using standard ISO methods except where indicated, and the standard deviations are provided in parentheses.

TABLE 1

Resin Composition

| | |
|---|---|
| BisGMA (Bisphenol A Diglycidyl ether dimethacrylate) | 3.0 weight % |
| Triethylene Glycol Dimethacrylate | 24.7 weight % |
| Ethoxylated Bisphenol A Dimethacrylate | 71.1 weight % |
| 2-Ethylhexyl-4-(dimethylamino)benzoate | 0.49 weight % |
| Camphorquinone | 0.17 weight % |
| 2-Hydroxy-4-methoxy Benzophenone | 0.49 weight % |
| (BHT) Butylated Hydroxytoluene | 0.05 weight % |
| Total | 100 |

TABLE 2

Filler Composition

| | |
|---|---|
| Barium Aluminum Borosilicate, silanated | 91.4 weight % |
| 20 nm[1] Hydrophobic fumed silica (TS-530)[2] | 4.3 weight % |
| 40 nm[1] Fumed Silica, silanated (OX-50)[3] | 4.3 weight % |
| Total | 100 |

[1]average particle size
[2]Degussa Corp., Ridgefield Park, N.J.
[3]Degussa Corp., Ridgefield Park, N.J.

It should be appreciated that alternative monomers to those listed in Table 1 above may be utilized in the resin composition. For example, diethylene glycol dimethacrylate, tetraethylene glycol dimethacrylate, 1,6-hexanediol dimethacrylate, 1,12-dodecanediol dimethacrylate, diurethane dimethacrylate (Rohamere 6661-0, Huls America, Somerset N.J.), trimethylolpropane trimethacrylate, glyceryl dimethacrylate, neopentylglycol dimethacrylate. Similarly, with respect to the filler components listed in Table 2 above, alternative filler components may be utilized for the filler composition. For example, inorganic glasses and crystalline compounds such as: quartz, cristoballite, silica, alumina, glass ceramics such as aluminosilicate glass ceramic, zirconium silicate, strontium aluminumborosilicate; and organic materials such as splintered pre-polymerized particles used for the preparation of inhomogeneous microfill dental composites.

TABLE 3

Physical Properties of Composites

| | Control Sample 1 | Test Sample 2 | Test Sample 3 |
|---|---|---|---|
| % Rheological Modifier | 0 | 0.5[1] | 1.0[2] |
| Wt. % Filler Load | 77.0 | 77.0 | 77.0 |
| Depth of Cure (mm) at 600 mw/cm², 4 mm diameter | 4.7 (0.1) | 5.0 (0) | 4.52 (0) |
| Rockwell Hardness (15T)[3] | 79.7 (0.6) | 78.5 (0.4) | 76.8 (0.8) |
| Compressive Strength (MPa) | 379 (20) | 356 (24) | 273 (36) |
| Flexural Strength (MPa) | 137 (23) | 119 (23) | 120 (18) |
| Flexural Modulus (MPa) | 10,192 (599) | 10,164 (594) | 9,481 (978) |
| % Volumetric Shrinkage[4] | 3.14 (0.03) | 1.76 (0.26) | 1.48 (0.08) |
| Penetrometer (mm)[5] 0 g, (Needle, 1 mm) | 4.2 (0.1) | 2.1 (0.1) | 2.0 (0.1) |
| G' at 10 ksec (KPa) | 100 | 4,500 | 7,410 |
| Normal Force (g)[6] | 40 | 737 | 1,330 |

[1]BYK ®-405, BYK Chemie USA, Wallingford, CT
[2]Thixatrol ® VF-10, Rheox Corp. Hightstown, NJ
[3]Average of 3 measurements on the surface of a cylindrical sample 10 mm in diameter and 4 mm in height. The samples were light cured for 40 seconds, and stored in water for 24 hours at 37° C. prior to measurement.
[4]Buoyancy method in water was used. The shrinkage was measured by the difference of densities before and after cure for a 1 g disk-shaped sample. The average of 3 samples is reported.
[5]Precision Penetrometer (GCA Corp., Chicago, IL) with a 1 mm needle was used with no additional weight (0 g). The paste was placed in a mold 10 mm in diameter and 8 mm in height. Penetration was performed for 10 seconds. An average of 3 measurements is reported.
[6]Elastic modulus (G') of uncured paste is measured using an SR-200 stress rheometer (Rheometrics Scientific, Piscataway, NJ) in the plate-plate configuration. The plate diameter was 10 mm with a gap spacing of 0.5 mm and the plate surfaces were sandblasted with 100 micron alumina. The measurement was made in the oscillatory mode at 0.1 rad./sec at 0.5% strain max. at 30° C. An initial weight of approximately 2 kg is applied on the composite in the axial direction to allow it to conform to the dimensions of the gap. When the 0.5 mm gap is reached, the Normal Force is the paste resistance in the axial direction when the paste is allowed to relax for 10 ksec after application of the initial weight.

The properties shown in Table 3 demonstrate that the use of the rheological modifier in test samples 2 and 3 reduced volumetric shrinkage by over 50% in comparison to the composite of control sample 1, which did not contain a modifier according to the present invention. By adding the rheological modifier according to the principles of the present invention, a volumetric shrinkage of less than about 2% may be achieved. In addition, the elastic modulus (G') of the uncured composites containing a theological modifier were increased considerably, resulting in increased condensability. Furthermore, the depth of cure and other critical properties of the composites, such as hardness and flexural strength, were not negatively impacted to any appreciable extent by the addition of the modifiers.

Dental Restorative Composite with Dispersant

Inclusion of a novel dispersant in dental composite formulations of the present invention results in increased filler loading and decreased viscosity, which after curing provides a dental restorative with reduced shrinkage, a lower coefficient of thermal expansion and generally improved physical properties. Suitable dispersants useful in the present invention are phosphoric acid esters (including mono-, di- and tri-esters). Particularly, phosphoric acid esters useful in the present invention are selected from the following: a) a phosphoric acid ester containing a carboxylic acid ester group and an ether group, and b) a phosphoric acid ester containing a carboxylic acid ester group and not containing an ether group. These dispersants are effective with nonaqueous, highly-filled suspensions containing polymerizable groups (e.g., acrylic and methacrylate esters) used for dental purposes and, more particularly, with highly-filled glass suspensions containing methacrylate resins. The dispersants useful in the present invention preferably comprise 5 weight percent or less of the composite paste. To obtain good uniformity of distribution of the dispersant in the final composite paste, the dispersant is first mixed with the resin, followed by the slow addition of the filler material.

In one embodiment of the present invention, the dispersant is a phosphoric acid ester with the following structure:

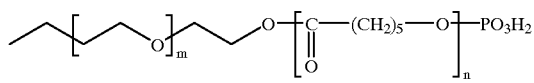

where n is equal to 5 to 10 and m is equal to 1 to 20.

The presence of the carboxylic acid ester group of the dispersant of the present invention results in excellent compatibility with (meth)acrylate-based resin systems. In a preferred embodiment of the present invention, the dispersant with the structure described by Formula 3 has a value m of 1 to 2 and a value n of 5 to 9. In a further preferred embodiment, the Formula 3 dispersant is preferably about 0.5 to about 3.5 weight percent of the composite paste. The following examples will further illustrate this aspect of the present invention.

EXAMPLE 2

Three samples (test samples 4–6) incorporating the above described Formula 3 dispersant were prepared according to the following method. A methacrylate resin, as described in Table 1 above, was introduced into a planetary mixer and thermostated to 50° C. For test samples 4–6, a phosphate ester with the structure described above in Formula 3 having a value m of 1 and a value n of 5–10 was added to the resin. The dispersant tested was obtained from BYK Chemie USA, Wallingford, Conn., under the trade name Disperbyk®-111 which may be disclosed in U.S. Pat. No. 5,151,218, the entire disclosure of which is hereby incorporated by reference. The mixer was started for about 5 minutes to mix the resin phase and then the filler containing the physically admixed components listed in Table 2 above was slowly added over a period of about 3 hours. Mixing was continued for another hour and the resultant paste was deaerated under attenuated oxygen pressure. Table 4 details the physical properties of the three test sample pastes prepared along with the properties of control sample 1. All measurements were carried out using standard ISO methods except where indicated, and the standard deviations are provided in parentheses.

TABLE 4

Physical Properties of Composites

|  | Control Sample 1 | Test Sample 4 | Test Sample 5 | Test Sample 6 |
|---|---|---|---|---|
| Formula 3 Dispersant[1] Wt. % | 0.0 | 0.8 | 1.5 | 3.0 |
| Wt. % Filler Load (Vol. % Load) | 77 (57.5) | 78.5 | 80 (61.7) | 82 (64.9) |
| Depth of Cure at 600 mw/cm$^2$, 4 mm diameter | 4.7 (0.1) | 4.96 (0.1) | 4.5 (0.1) | 4.65 (0.1) |
| Rockwell Hardness (15T)[2] | 79.7 (0.6) | 81.0 (1.1) | 82.2 (0.3) | 78.7 (0.7) |
| Compressive Strength (MPa) | 379 (20) | 320 (23) | 343 (25) | 325 (15) |
| Flexural Strength (MPa) | 137 (23) | 130 (16) | 118 (12) | 104 (9) |
| Flexural Modulus (MPa) | 10,192 (599) | 10,918 (433) | 10,175 (468) | 9,272 (509) |
| % Volumetric Shrinkage[3] | 3.14 (0.03) | 2.92 (0.07) | 2.44 (0.25) | 2.11 (0.06) |
| Penetrometer (mm)[4] 0 g, (Needle, 1 mm) | 4.2 (0.1) | 3.2 (0.1) | 2.3 (0.1) | 2.9 (0.2) |
| Penetrometer (mm)[5] 0 g, (Flathead, 1 mm) | 2.8 (0.2) | 1.5 (0.1) | 1.6 (0.1) | 1.2 (0.1) |

[1]Disperbyk ®-111, BYK Chemie USA, Wallingford, CT
[2]Average of 3 measurements on the surface of a cylindrical sample 10 mm in diameter and 4 mm in height. The samples were light cured for 40 seconds, and stored in water for 24 hours at 37° C. prior to measurement.
[3]Buoyancy method in water was used. The shrinkage was measured by the difference of densities before and after cure for a 1 g disk-shaped sample. The average of 3 samples is reported.
[4]Precision Penetrometer (GCA Corp., Chicago, IL) with a 1 mm needle was used with no additional weight (0 g). The paste was placed in a mold 10 mm in diameter and 8 mm in height. Penetration was performed for 10 seconds. An average of 3 measurements is reported.
[5]Same test as above, but using a flat head rather than a needle, to simulate the effect of the impact from dental instruments having a flat head on the composite.

A comparison of control sample 1 with test sample 5 demonstrates that the volume filler load may be increased from 57.5% to 61.7% (from 77 to 80 wt. %) by the addition of the phosphate ester while the viscosity remains similar to the viscosity of the control sample. The penetrometer reading is a measure of viscosity to a certain extent, but no direct relationship has been established. The G' aid Normal Force measurements, as reported in Table 3, although useful for composite pastes containing the rheological modifier, have proven unreliable when a dispersant is added to the paste. Table 4 further shows that the physical properties of the composite pastes were not negatively impacted by the addition the dispersant. Further increase of volume load to 64.9% (82 wt. %) as shown in test sample 6, although resulting in a decrease in flexural strength, provides physical properties that still satisfy the American Dental Association guidelines for restorative composites. The tests also demonstrate that a reduction of volumetric shrinkage of about 30% may be achieved by the volume load increase from 57.5% to 61.7%, as shown in test sample 5. This is expected to result in improved adaptation when placed in a tooth cavity and cured.

In another embodiment of the present invention, the dispersant is a phosphoric acid ester with the following structure:

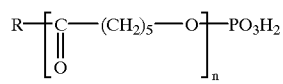

where R is a (meth)acrylate group functionalized radical.

Again, the presence of the carboxylic acid ester group of the above dispersant (Formula 4) results in excellent compatibility with (meth)acrylate-based resin systems. In a preferred embodiment, the above dispersant of the present invention having the structure shown in Formula 4, R is one of the following:

Compound 1: R=oxyethyl methacryloyl-

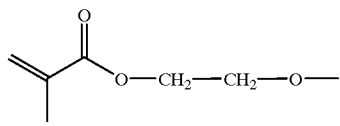

Compound 2: R=oxyethyl acryloyl-

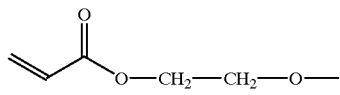

Compound 3: R=polyoxypropyl methacryloyl-

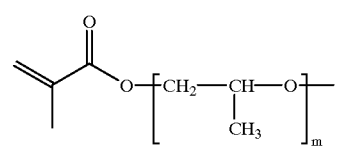

Compound 4: R=glyceryl dimethacryloyl-

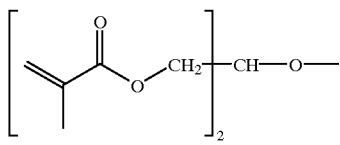

Compound 5: R=dipentaerythritol pentaacryloyl-

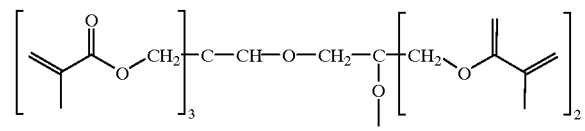

Each of Compounds 1–5 may be prepared in two steps. In the first step, the hydroxy functional methacrylate is condensed with caprolactone under ring-opening polymerization conditions in the presence of catalytic amounts of $SnCl_2$ to prepare a polyester. In the second step, the polyester is reacted with polyphosphoric acid (117.5% concentration) at 65° C. to give the phosphoric acid ester. By way of example, the reaction sequence is shown below for the preparation of the hydroxyethyl methacrylate (HEMA) derivative Compound 1:

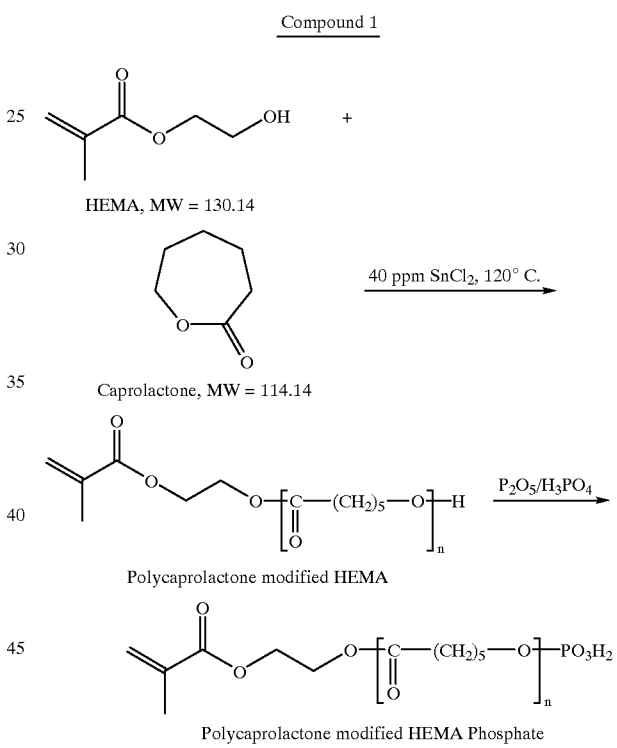

In a further preferred embodiment of the present invention, the Formula 4 dispersant is preferably added at about 0.5 to about 3.5 weight percent of the composite paste. The following examples will further illustrate this aspect of the present invention.

EXAMPLE 3

In a 4-neck reaction kettle containing an air flow tube, a thermocouple, a condenser and a stirrer, 26.0 parts by weight of hydroxyethyl methacrylate (HEMA) were combined with 114.1 parts by weight of caprolactone, 0.14 parts by weight of methyl ether of hydroquinone (MEHQ) and 0.007 parts by weight of stannous chloride under a flow of dry air. The mixture was thermostated at 120° C. and stirring was continued for 18 hours. The disappearance of the caprolactone was monitored with HPLC (High Pressure Liquid Chromatography) using a reverse phase column with 70/30 acetonitrile/water as eluant. The resultant liquid polycaprolactone-modified HEMA was essentially colorless.

In a three neck flask equipped with a stirrer and a condenser under a constant flow of dry air, 70.0 grams of the above product (polycaprolactone-modified HEMA) was combined with 8.45 grams of 117.5% phosphoric acid. The mixture was heated with stirring for 4 hours at 70° C. A light yellow oil resulted. Titration with 0.1N NaOH showed that the phosphoric acid ester was formed.

Various Formula 4 methacrylate derivatives prepared using the above procedures are listed in Table 5.

TABLE 5

Polycaprolactone-Modified Methacrylate Monophosphates

| Compound | Starting Material | Caprolactone: starting material (mole ratio) | Molecular Weight Average |
| --- | --- | --- | --- |
| 1a | Hydroxyethyl Methacrylate (HEMA) | 1:1 | 324 |
| 1b | HEMA | 2:1 | 438 |
| 1c | HEMA | 5:1 | 780 |
| 1d | HEMA | 7:1 | |
| 2 | Hydroxyethyl acrylate (HEA) | 5:1 | 766 |
| 3 | Polypropylene glycomethacrylate (PPGMA) | 5:1 | 713 |
| 4a | Glycerol Dimethacrylate (GDMA) | 2:1 | 536 |
| 4b | GDMA | 5:1 | 879 |

TABLE 5-continued

Polycaprolactone-Modified Methacrylate Monophosphates

| Compound | Starting Material | Caprolactone: starting material (mole ratio) | Molecular Weight Average |
| --- | --- | --- | --- |
| 5a | Dipentaerythritol pentaacrylate (DPEPA) | 2:1 | 713 |
| 5b | DPEPA | 5:1 | 1175 |

All of the above compounds may be used as dispersants in highly filled glass suspensions containing methacrylate resins. Nine test samples (test samples 7–15) were prepared according the following method. A methacrylate resin, as described in Table 1 above, was introduced into a planetary mixer and thermostated to 50° C. The phosphate ester with the structure described above by Formula 4 was then added to the resin so as to comprise 1.5 weight percent of the total resin/filler mixture with an 80 weight percent filler loading. The mixer was started for a few minutes to mix the resin phase and then the filler containing the physically admixed components listed in Table 2 above was slowly added over a period of about 3 hours. Mixing was continued for another hour and the resultant paste was deaerated under attenuated oxygen pressure. Table 6 details the physical properties of the Formula 4 test sample pastes (7–15) prepared along with the properties of control sample 1 and test sample 5 (containing a Formula 3 dispersant). All measurements were carried out using standard ISO methods except where indicated, and the standard deviations are provided in parentheses.

TABLE 6

Physical Properties of Pastes Prepared with Various Dispersants

| | Control Sample 1 | Test Sample 5 | Test Sample 7 | Test Sample 8 | Test Sample 9 | Test Sample 10 | Test Sample 11 | Test Sample 12 | Test Sample 13 | Test Sample 14 | Test Sample 15 |
| --- | --- | --- | --- | --- | --- | --- | --- | --- | --- | --- | --- |
| Dispersant, 1.5 Wt. % | None | Disperbyk ®-111 | 1b | 1c | 1d | 2 | 3 | 4a | 4b | 5a | 5b |
| Wt % Filler Load (Vol. % Load) | 77 | 80 | 80 | 80 | 80 | 80 | 80 | 80 | 80 | 80 | 80 |
| Depth of Cure at 600 mw/cm$^2$, 4 mm diameter | 4.7 (0.1) | 4.5 (0.1) | 4.2 (0.1) | 4.6 (0.1) | 4.0 (0.1) | 4.2 (0.1) | 3.9 (0.03) | 4.4 (0.1) | 4.1 (0.3) | 4.1 (0.1) | 4.5 (0.2) |
| Rockwell Hardness (15T)[1] | 79.7 (0.6) | 82.2 (0.3) | 84.4 (0.38) | 83.4 (0.1) | 82.4 (0.3) | 83.3 (0.3) | 83.1 (0.3) | 84.0 (0.5) | 83.9 (0.1) | 83.6 (0.4) | 83.3 (0.1) |
| Compressive Strength (MPa) | 379 (20) | 343 (25) | 290 (62) | 399 (21) | 375 (17) | 314 (29) | 341 (29) | 394 (43) | 408 (34) | 387 (27) | 381 (27) |
| Flexural Strength (MPa) | 137 (23) | 118 (12) | 124 (22) | 129 (12) | 120 (9) | 127 (14) | 110 (11) | 114 (22) | 125 (26) | 105 (12) | 106 (6) |
| Flexural Modulus (MPa) | 10,192 (599) | 10,175 (468) | 11,362 (773) | 11,189 (968) | 10,827 (1,035) | 12,187 (1,754) | 11,460 (1,045) | 11,977 (899) | 10,571 (2,051) | 12,404 (1,006) | 11,664 (619) |
| Penetrometer (mm)[2] 0 g, (Needle, 1 mm) | 4.2 (0.1) | 2.3 (0.1) | 3.6 (0.1) | >8.0 | >8.0 | >8.0 | 5.5 (0.1) | 2.1 (0.2) | 6.2 (0.2) | 2.7 (0.2) | 3.0 (0.1) |
| Penetrometer (mm)[3] 0 g, (Flathead, 1 mm) | 2.8 (0.2) | 1.6 (0.1) | 2.3 (0.2) | >8.0 | >8.0 | 7.1 (0.1) | 2.3 (0.1) | 1.3 (0.1) | 4.3 (0.1) | 1.5 (0.1) | 1.0 (0.1) |
| Penetrometer (mm)[3] 0 g, (Flathead, 2 mm) | | | | 5.7 (0.1) | 4.5 (0.1) | | | | | | |

[1]Average of 3 measurements on the surface of a cylindrical sample 10 mm in diameter and 4 mm in height. The samples were light cured for 40 seconds, and stored in water for 24 hours at 37° C. prior to measurement.
[2]Precision Penetrometer (GCA Corp., Chicago, IL) with a 1 mm needle was used with no additional weight (0 g). The paste was placed in a mold 10 mm in diameter and 8 mm in height. Penetration was performed for 10 seconds. An average of 3 measurements is reported.
[3]Same test as above, but using a flat head rather than a needle, to simulate the effect of the impact from dental instruments having a flat head on the composite.

The properties shown in Table 6 demonstrate that there is a dramatic reduction of viscosity of the pastes where the phosphate esters of Compound 1 are included. As stated previously, the penetrometer test is indicative of the viscosity of the paste, although not directly related. There is also demonstrated a substantial increase of the dispersant effect (decrease in viscosity) of the Formula 4 dispersants when compared with the commercial material Disperbyk®-111 (Formula 3 dispersant). Furthermore, the physical properties of the composites are not significantly reduced by the addition of the polycaprolactone-modified methacrylate monophosphates.

As a further comparison, the most efficient dispersant listed above, Compound 1c, was also formulated in pastes at different loads and amounts (test samples 16–18). The results of test samples 8 and 16–18 are listed in Table 7.

TABLE 7

Compound 1c at Various Loadings

|  | Test Sample 8 | Test Sample 16 | Test Sample 17 | Test Sample 18 |
| --- | --- | --- | --- | --- |
| Wt. % Compound 1c dispersant | 1.5 | 1.5 | 2.0 | 3.0 |
| Wt. % Filler Load | 80 | 76 | 82 | 82 |
| Penetrometer (mm) 0 g, (Flathead, 1 mm) | >8.0 | — | 4.4 (0.2) | >8.0 |
| Penetrometer (mm) 0 g, (Flathead, 2 mm) | 6.6 (0.0) | 4.6 (0.2) | 2.0 (0.2) | 5.1 (0.0) |
| Depth of Cure at 600 mw/cm2, 4 mm diameter | 4.6 (0.1) | 4.8 (0.1) | 4.5 (0.1) | 4.2 (0.1) |
| % Volumetric Shrinkage | 2.60 (0.18) | 2.91 (0.4) | 2.37 (0.08) | 2.50 (0.25) |
| Rockwell Hardness 15T | 83.4 (0.1) | 80.9 (0.5) | 84.7 (0.4) | 82.2 (0.2) |
| Compressive Strength (MPa) | 399 (21) | 350 (28) | 312 (48) | 274 (25) |
| Flexural Strength (MPa) | 129 (12) | 139 (13) | 132 (17) | 105 (14) |
| Flexural Modulus (MPa) | 11,189 (968) | 12,297 (727) | 12,159 (1,038) | 10,471 (741) |

The results shown in Table 7 demonstrate that a low relative viscosity paste having acceptable physical properties may be prepared at 82% filler loading with only 2% Formula 4 dispersant based on a 1c Compound. In contrast, pastes incorporating no dispersant cannot be made with a filler loading above 77%. See Control Sample 1 in Table 6.

Dental Restorative Composite with Fluorocopolymer

In a further aspect of the present invention, an effective amount of a known fluorocopolymer material such as that disclosed in Yamabe et al. U.S. Pat. No. 4,345,057, the entire disclosure of which is incorporated herein by reference, is added to the resin/filler mixture to provide a dental restorative composite of the present invention that possesses improved wear properties when used in the mouth. The material described in the Yamabe et al. patent and to be used as an additive for the dental restorative of the present invention is a fluorocopolymer of a fluoroolefin, a cyclohexyl vinyl ether, an alkyl vinyl ether and a hydroxyalkyl vinyl ether. For use in the present invention, the fluorocopolymer additive comprises the above four components at ratios of about 40–60 mole % fluoroolefin units, about 5–45 mole % cyclohexyl vinyl ether units, about 5–45 mole % alkyl vinyl ether units and about 3–15 mole % hydroxyalkyl vinyl ether units. Preferably, the fluorocopolymer additive comprises the above four components at ratios of about 45–55 mole % fluoroolefin units, about 10–30 mole % cyclohexyl vinyl ether units, about 10–35 mole % alkyl vinyl ether units and about 5–13 mole % hydroxyalkyl vinyl ether units. In a preferred embodiment of the present invention, the fluorocopolymer comprises about 10 weight percent or less of the composite paste, and more preferably, less than 1 weight percent.

The fluorocopolymer used in the present invention is soluble in (meth)acrylate resins, in particular dimethacrylate resins, does not interfere in a deleterious manner with the curing of the paste and does not negatively influence the physical and aesthetic properties of the resultant composite after curing. The following examples will further illustrate this aspect of the present invention.

EXAMPLE 4

Four samples (test samples 19–22) incorporating a fluorocopolymer into the composite resin of the present invention were prepared according to the following method. A methacrylate resin, as described in Table 1 above, was introduced in a planetary mixer and thermostated to 50° C. A fluorocopolymer LF-200 (supplied by Zeneca Resins Co., Wilmington, Mass.) was added to the resin. A suitable alternative fluorocopolymer is X-910LM (also available from Zeneca Resins). Initially, the fluorocopolymer is supplied as a 60% solution in xylene, but the xylene is evaporated in a vacuum at 80° C. and 0.1 Torr. The resin mix used in test samples 19–22 contained the evaporated fluorocopolymer in an amount of 3.6 wt. % and the resin of Table 1 in an amount of 96.4 wt. %. The mixer was started for about five minutes to mix the resin phase and then the filler containing the physically admixed components listed in Table 2 above was slowly added over a period of 3–5 hours to a filler loading of 77 wt. %. Mixing was continued for another hour and the resultant paste was deaerated under attenuated oxygen pressure. Table 8 details the physical properties of the test sample pastes 19–22 prepared along with the properties of control sample 1. All measurements were carried out using standard ISO methods except where indicated, and the standard deviations are provided in parentheses.

TABLE 8

Physical Properties of Composites

| | Control Sample 1 | Test Sample 19 | Test Sample 20 | Test Sample 21 | Test Sample 22 |
|---|---|---|---|---|---|
| Wt. % Fluoro-copolymer[1] | 0 | 0.28 | 0.55 | 0.83 | 1.00 |
| Wt. % Filler Load | 77.0 | 77.0 | 77.0 | 77.0 | 77.0 |
| Depth of Cure (mm)[2] at 600 mw/cm$^2$ (4 mm diameter) | 4.7 (0.1) | 4.49 (0.02) | 4.12 (0.01) | 4.26 (0.20) | 4.60 (0.0) |
| Translucency (1 mm) | 25.2 | 25.6 | 23.6 | 23.4 | 22.1 |
| Rockwell Hardness (15T)[2] | 79.7 (0.6) | 82.4 (0.13) | 82.0 (0.1) | 82.6 (0.3) | 81.2 (0.5) |
| Compressive Strength (MPa) | 379 (20) | 383 (35) | 392 (27) | 384 (37) | 311 (25) |
| Flexural Strength (MPa) | 137 (23) | 132 (17) | 139 (16) | 126 (9) | 121 (12) |
| Flexural Modulus (MPa) | 10,192 (599) | 10,828 (954) | 10,800 (950) | 10,800 (900) | 11,070 (541) |
| Penetrometer (mm)[4], 0 g (Needle, 1 mm) | 4.2 (0.1) | 3.7 (0.2) | 5.7 (0.2) | 4.0 (0.3) | 3.3 (0.2) |
| Penetrometer (mm)[3], 0 g (Flathead, 1 mm) | 2.8 (0.2) | 3.3 (0.3) | 1.6 (0.1) | 1.5 (0.3) | 1.2 (0.1) |
| 3 Body Wear Rate (cc/cycle)[4] | $9.1 \times 10^{-9}$ | | $1.2 \times 10^{-8}$ | $3.5 \times 10^{-9}$ | $3.95 \times 10^{-9}$ |
| Number of Cycles Run | $2.0 \times 10^5$ | | $1.2 \times 10^5$ | $3.0 \times 10^5$ | $1.8 \times 10^5$ |

[1] Lumiflon LF-200, Zeneca Resins, Wilmington, MA
[2] Average of 3 measurements on the surface of a cylindrical sample 10 mm in diameter and 4 mm in height. The samples were light cured for 40 seconds, and stored in water for 24 hours at 37° C. prior to measurement.
[3] Precision Penetrometer (GCA Corp., Chicago, IL) with a 1 mm needle or a 1 mm flathead was used with no additional weight (0 g). The paste was placed in a mold 10 mm in diameter and 8 mm in height. Penetration was performed for 10 seconds. An average of 3 measurements is reported.
[4] The wear test was performed in the 3-body wear mode using specialized apparatus. A disk of the cured composite, 26 mm in diameter and 1.0 mm thick, was abraded against the flat end of a 13 mm in diameter glass ceramic rod (Macor, Dow Corning Corp., Corning, NY) having equivalent hardness to enamel inside a cup. The cup was charged with 10 g polyethyl methacrylate beads (Ionac 26F, Sybron Chemicals Corp., Birmingham, NJ) suspended in water at a ratio of 1:1 to simulate the food bolus. The composite disk was rotated at about 2 Hz while the rod came in contact with the disk surface in an up and down motion of 0.33 Hz using a vertically positioned cam shaft. The maximum contact pressure was 35 MPa. The bead slurry was changed every 10 kcycles and the weight of the disk was measured every 30 kcycles.

The properties shown in Table 8 demonstrate that the addition of a soluble fluorocopolymer at a total concentration of less than 1 weight percent of the resin/filler mixture reduces the wear of the composite, in particular reduces the wear rate in a three body wear test to less than half the value for the composite without the addition. Furthermore, the physical and aesthetic properties of the composite are not significantly effected. Namely, the translucency, depth of cure and flexural strength and modulus of the resulting composite remained about the same as that of the composite not containing the fluorocopolymer additive (Control Sample 1).

Dental Restorative Composite with Rheological Modifier, Dispersant and Fluorocopolymer Additive The addition of a combination of the described additives provides a dental restorative composite with superior properties to that of a composite with no such additives. Eight test samples were prepared according to the above described methods. Test samples 23 and 24 combine the resin/filler mixture with a Formula 1 rheological modifier and Formula 3 dispersant. Test samples 25–27 combine the resin/filler mixture with varying amounts of a Formula 1 rheological modifier and varying amounts of a Formula 4 dispersant based on Compound 1c. Test samples 28–30 also add a fluorocopolymer to one of the above combinations. Table 9 details the physical properties of the sample pastes prepared.

TABLE 9

Properties of Pastes with a Combination of Additives

| | Control Sample 1 | Test Sample 23 | Test Sample 24 | Test Sample 25 | Test Sample 26 | Test Sample 27 | Test Sample 28 | Test Sample 29 | Test Sample 30 |
|---|---|---|---|---|---|---|---|---|---|
| Wt. % Formula 1 Rheological Modifier | 0 | 0.5 | 0.45 | 0.3 | 0.3 | 0.5 | 0.5 | 0.3 | 0.2 |
| Wt. % Formula 3 Dispersant | 0 | 2.0 | 1.45 | 0 | 0 | 0 | 0 | 0 | 2.0 |
| Wt. % Formula 4 Dispersant of Compound 1c | 0 | 0 | 0 | 3.00 | 1.50 | 2.0 | 2.0 | 2.0 | 0 |
| Wt. % Fluorocopolymer | 0 | 0 | 0 | 0 | 0 | 0 | 0.40 | 0.72 | 0.72 |
| Wt. % Filler Load | 77 | 80 | 80 | 82 | 80 | 80 | 80 | 80 | 80 |
| Depth of Cure (mm) at 600 mw/cm$^2$ (4 mm diameter) | 4.7 (0.1) | 4.2 (0.1) | 4.68 (0.04) | 4.29 (0.10) | 4.1 (0.1) | 4.1 (0.0) | 3.8 (0.1) | 4.1 (0.0) | 3.8 (0.1) |
| Rockwell Hardness (15T) | 79.7 (0.6) | 81.3 (0.19) | 80.7 | 83.1 (0.3) | 83.2 (0.2) | 83.2 (0.13) | 81.9 (0.16) | 81.6 (0.3) | 81.0 (0.5) |
| Compressive Strength (MPa) | 379 (20) | 302 (21) | 317 (27) | 285 (34) | 343 (33) | 285 (16) | 310 (22) | 338 (18) | 297 (26) |
| Flexural Strength (MPa) | 137 (23) | 98 (11) | 120 (11) | 121 (14) | 110 (15) | 108 (9) | 117 (9) | 122 (4) | 117 (15) |
| Flexural Modulus (MPa) | 10,192 (599) | 9,979 (644) | 9,660 (708) | 11,080 (619) | 11,693 (664) | 10,763 (898) | 10,599 (480) | 11,392 (639) | 9,763 (1,170) |
| % Volumetric Shrinkage | 3.14 (0.03) | | 1.54 (0.17) | 1.75 (0.04) | 1.58 (0.48) | 1.53 (0.26) | 0.86 (0.33) | 1.74 (0.16) | 1.77 (0) |
| G' at 10 ksec (KPa) | 100 | | 4,800 | 1,440 | 1,440 | 3,390 | 3,880 | 1,710 | |
| Normal Force (g) | 40 | | 700 | 565 | 850 | 1,315 | 1,306 | 1,150 | |
| Penetrometer (mm), 150 g Needle, 1 mm | >8.0 | 4.7 (0.1) | 5.1 (0.1) | 4.8 (0.2) | 7.4 (0.2) | 4.45 (0.2) | 3.4 (0.1) | 4.5 (0.1) | 5.0 (0.1) |
| 3 Body Wear Rate (cc/cycle)$^5$ | 9.1 × 10$^{-9}$ | | | | 1.05 × 10$^{-8}$ | 4.09 × 10$^{-9}$ | 1.10 × 10$^{-8}$ | 4.50 × 10$^{-9}$ | 4.09 × 10$^{-9}$ |
| Number of Cycles Run | 2.0 × 10$^5$ | | | | 2.0 × 10$^5$ | 3.0 × 10$^{-5}$ | 2.42 × 10$^{-5}$ | 3.0 × 10$^5$ | 3.0 × 10$^5$ |

The various compositions were tested to determine the amount of each additive required to optimize condensability, shrinkage, wear and physical properties. It was found that there is substantial interplay between the rheological modifier and the fluorocopolymer, because both additives affect the thixotropic properties of the composite. For example, the rheological modifier thickens and renders the composite paste thixotropic, while the dispersant makes the paste thinner and allows for higher loading. The blending of the effects of the rheological modifier and the dispersant provides a composite material with improved handling. While in the abstract these different additives appear to have a contradictory effect, the sum total effect is a superior dental composite material with improved handling. Thus, overall, the various properties of a composite paste are optimized when all three additives are combined within the resin/filler mixture. As shown in Table 9, test samples 27 and 28 provided the best overall properties with the additives present in the noted amounts.

In one of its most preferred forms, the dental composite of the present invention is comprised of about 80 wt. % filler as described in Table 2, about 0.2 to about 0.3 wt. % of a Formula 1 rheological modifier, about 2 wt. % of a Formula 3 dispersant or a Formula 4 dispersant based on Compound 1c, about 0.72 wt. % of a fluorocopolymer, and the balance being the resin as described in Table 1. This formulation is believed to have a layer depth limit of about 4 mm. Where greater layer depths are desired, up to 5 mm or more, it is advantageous to utilize a formulation that does not include the fluorocopolymer component, although sacrificing the improved wear resistance that the fluorocopolymer provides. In all other respects, the above preferred formulation would remain the same.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, the quantity of the rheological modifier, dispersant and/or fluorocopolymer to be added to the resin/filler mixture will vary based on the particular compositions used for the resin and the filler. The invention in its broader aspects is therefore not limited to the specific details, representative method and illustrative examples shown and described. Accordingly, departures may be made from such details without departing from the scope or spirit of applicant's general inventive concept.

What is claimed is:

1. A dental restorative composition comprised of:
   a filler;
   a polymerizable acrylic monomer; and
   a fluorocopolymer of a fluoroolefin, a cyclohexyl vinyl ether, an alkyl vinyl ether and a hydroxyalkyl vinyl ether.

2. The dental restorative composition of claim 1, wherein the fluorocopolymer comprises about 10 weight percent or less of the dental restorative composition.

3. The dental restorative composition of claim 1, wherein the fluorocopolymer comprises about 1 weight percent or less of the dental restorative composition.

4. The dental restorative composition of claim 1, wherein the fluorocopolymer is comprised of about 45–55 mole percent fluoroolefin units, about 10–30 mole percent cyclohexyl vinyl ether units, about 10–35 mole percent alkyl vinyl ether units and about 5–13 mole percent hydroxyalkyl vinyl ether units.

5. A dental restorative composition comprised of:
   a filler;
   a polymerizable acrylic monomer; and
   a fluorocopolymer of a fluoroolefin, a cyclohexyl vinyl ether, an alkyl vinyl ether and a hydroxyalkyl vinyl ether, wherein the fluorocopolymer comprised of about 40–60 mole percent fluoroolefin units, about 5–45 mole percent cyclohexyl vinyl ether units, about 5–45 mole percent alkyl vinyl ether units and about 3–15 mole percent hydroxyalkyl vinyl ether units.

6. The dental restorative composition of claim 5, wherein the fluorocopolymer comprises about 10 weight percent or less of the dental restorative composition.

7. The dental restorative composition of claim 5, wherein the fluorocopolymer comprises 1 weight percent or less of the dental restorative composition.

8. A method of restoring a tooth comprising the steps of:
   preparing the tooth for restoration; and
   applying to the prepared tooth the dental restorative composite of claim 1.

9. The dental restorative composition of claim 1, further comprising a rheological modifier in an amount effective to reduce the volumetric shrinkage of the dental restorative during polymerization thereof.

10. The dental restorative composition of claim 1, further comprising a phosphoric acid ester dispersant.

11. The dental restorative composition of claim 10, wherein the dispersant is a polycaprolactone-modified methacrylate monophosphate.

12. The dental restorative composition of claim 1, further comprising:
    a rheological modifier in an amount effective to reduce the volumetric shrinkage of the dental restorative during polymerization thereof; and
    a phosphoric acid ester dispersant.

13. The dental restorative composition of claim 5, further comprising a rheological modifier in an amount effective to reduce the volumetric shrinkage of the dental restorative during polymerization thereof.

14. The dental restorative composition of claim 5, further comprising a phosphoric acid ester dispersant.

15. The dental restorative composition of claim 14, wherein the dispersant is a polycaprolactone-modified methacrylate monophosphate.

16. The dental restorative composition of claim 5, further comprising:
    a rheological modifier in an amount effective to reduce the volumetric shrinkage of the dental restorative during polymerization thereof; and
    a phosphoric acid ester dispersant.

* * * * *

UNITED STATES PATENT AND TRADEMARK OFFICE
CERTIFICATE OF CORRECTION

PATENT NO. : 6,384,106 B1 Page 1 of 1
DATED : May 7, 2002
INVENTOR(S) : Christos Angeletakis It is certified that error appears in the above-identified patent and that said Letters Patent is hereby corrected as shown below:

Column 8,
Line 54, reads "theological" and should read -- rheological --.

Column 11,
Line 6, reads "addition the dispersant" and should read -- addition of the dispersant --.
Line 20, is missing the subtitle "Formula 4:"

Column 12,
Line 21, reads "Compound 1" and should be moved to Column 12, line 48 reading -- Compound 1: Polycaprolactone --.

Column 19,
Line 30, reads "Needle, 1mm)" and should read -- (Needle, 1mm) --.

Column 20,
Line 31, reads "$10^{-5}$" and should read -- $10^5$ --.

Signed and Sealed this

Eleventh Day of February, 2003

JAMES E. ROGAN
*Director of the United States Patent and Trademark Office*